(12) United States Patent
Nishigaki et al.

(10) Patent No.: US 7,521,703 B2
(45) Date of Patent: Apr. 21, 2009

(54) AUTOMATIC ANALYZER

(75) Inventors: Kenichi Nishigaki, Hitachinaka (JP); Masato Ishizawa, Hitachinaka (JP); Shigenori Watari, Hitachinaka (JP)

(73) Assignee: Hitachi High-Technologies Corp., Tokyo (JP)

( * ) Notice: Subject to any disclaimer, the term of this patent is extended or adjusted under 35 U.S.C. 154(b) by 86 days.

(21) Appl. No.: 11/653,949

(22) Filed: Jan. 17, 2007

(65) Prior Publication Data

US 2007/0181787 A1 Aug. 9, 2007

(30) Foreign Application Priority Data

Jan. 23, 2006 (JP) .............................. 2006-013962

(51) Int. Cl.
*G01J 1/42* (2006.01)
(52) U.S. Cl. .................. 250/577; 250/576; 250/227.25; 250/227.14
(58) Field of Classification Search ................. 250/573, 250/576, 577, 227.25; 73/293
See application file for complete search history.

(56) References Cited

U.S. PATENT DOCUMENTS 4,121,103 A * 10/1978 Calhoun ...................... 250/343
4,690,900 A    9/1987 Kimmo et al.
5,557,368 A * 9/1996 Endo et al. ..................... 399/27
5,689,290 A * 11/1997 Saito et al. ...................... 347/7
5,747,824 A * 5/1998 Jung et al. ................... 250/577
6,723,287 B1    4/2004 Ootatsume et al.

FOREIGN PATENT DOCUMENTS

| EP | 107 410 | 5/1984 |
|---|---|---|
| EP | 303 707 | 2/1989 |
| JP | 09-080055 | 3/1997 |
| JP | 2000-258433 | 9/2000 |

* cited by examiner

*Primary Examiner*—Georgia Y Epps
*Assistant Examiner*—Tony Ko
(74) *Attorney, Agent, or Firm*—Mattingly, Stanger, Malur & Brundidge, PC

(57) ABSTRACT

In an automatic analyzer which includes a reaction container which contains reaction solution therein, a light source which emit light to be transmitted through the reaction solution, a spectral detector which measures the light transmitted through the reaction solution, a memory which stores light measurement data measured by the spectral detector and a CPU which calculates the light measurement data stored in the memory to obtain a light intensity, wherein the spectral detector measures the light over an entirety of an area from one end to the other end of the reaction container at a portion where the reaction solution reserves, the memory stores the light measurement data measured by the spectral detector, and light measurement data in an area where the reaction solution exists is obtained from the memory to calculate a light intensity.

6 Claims, 4 Drawing Sheets

AUTOMATIC ANALYZER

BACKGROUND OF THE INVENTION

1. Field of the Invention

The present invention relates to an automatic analyzer which conducts the qualitative and quantitative analysis of a biological sample such as blood or urine. In particular, the present invention relates to an automatic analyzer of a type where a light source and a spectral detector are disposed so as to oppose to each other via a reaction container thereby to measure a quantity of light transmitted through the reaction container.

2. Description of the Related Art

The automatic analyzer detects the presence/non-presence or measures a density of an objective component(s) within a biological sample such as blood or urine. Since the automatic analyzer is higher in the analyzing speed and the analyzing accuracy (reproducibility) as compared with a case where a medical technologist measures manually, the automatic analyzers have widely spread mainly in large hospitals and medical laboratories.

The automatic analyzer is arranged to measure absorbance in a manner that the optical axis of a transmission light is shifted sequentially to an adjacent reaction container while rotating reaction containers which are continuously disposed in a circumferential manner. In order to measure the absorbance accurately, the timing of the light measurement is required to be synchronized with the rotation of the reaction containers.

As a technique for satisfying such a requirement, JP-A-9-80055 discloses that detection plates (reaction container position detection means) having the same number as that of the reaction containers are provided in a circumferential manner concentrically above the reaction containers thereby to detect the positions of the reaction containers. JP-A-2000-258433 discloses a technique that the light measurement starting position of a reaction container is determined in accordance with an encoder signal from a direct drive motor having an encoder.

SUMMARY OF THE INVENTION

According to the technique disclosed in JP-A-9-80055, the detection plate of the reaction container position detection means interrupts a sensor to detect the position of the reaction container thereby to measure the light. According to this method, the detection plates are required to have the number corresponding to that of the reaction containers and further a space for the detection plates and the sensors for the detection plates is required.

In each of JP-A-9-80055 and JP-A-2000-258433, the accuracy is required between the reaction container and the detection plate. The demand for improving such an accuracy having been increasing due to the miniaturization of the reaction container and the enlargement of the reaction disc which are caused by the increase of the number of the reaction containers due to the increase of the analysis processing ability.

Further, in each of JP-A-9-80055 and JP-A-2000-258433, the light intensity is measured over a predetermined area after receiving a signal from the detection plate or the encoder, and then the measured light intensities are averaged to determine the absorbance. According to this method, even in a case where a foreign matter exists within the reaction solution, the light intensities of the transmission light cutoff by the foreign matter are also averaged. As a result, the absorbance of the reaction solution within the reaction containers is erroneously read as a higher value.

An object of the invention is to provide an automatic analyzer which can measure an absorbance without erroneous.

In order to attain the aforesaid object, the present invention is arranged in a manner that in an automatic analyzer which measures light transmitted through reaction solution within a reaction container, the transmission light is measured over the entire area from one end to the other end of the reaction container at a portion where the reaction solution is accumulated.

According to the present invention, an automatic analyzer which can measure an absorbance without erroneous can be provided even if a foreign matter exists within the reaction solution or reagent is not mixed sufficiently.

Further, the present invention can eliminate the detection plate which was necessary for detecting the position of the reaction container.

DESCRIPTION OF THE PREFERRED EMBODIMENTS

Embodiments of the present invention will be explained in detail with reference to the accompanying drawings.

First, an automatic analyzer shown in FIG. 1 according to the embodiment of the present invention will be explained schematically.

Figure 1:
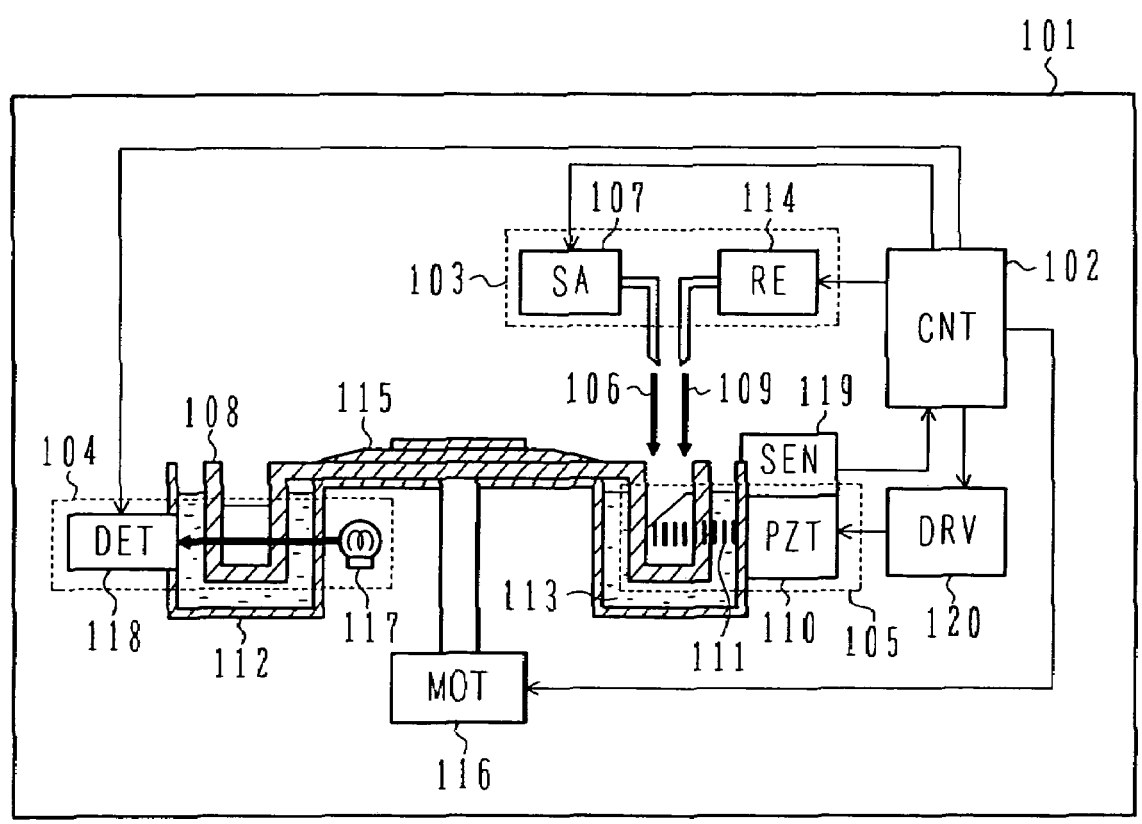
FIG. 1 is a diagram showing the schematic configuration of an automatic analyzer according to an embodiment of the present invention.

In FIG. 1, an automatic analyzer 101 is configured by a control unit 102, a housing unit 103, an analyzing unit 104 and a stirring unit 105.

The control unit 102 controls the operations of respective portions by means of an electronic circuit and a memory device for controlling the operations of the respective portions in detail.

The housing unit 103 is configured by a sample housing unit 107 in which sample 106 is contained and a reagent housing unit 114 in which reagent 109 is contained.

The analyzing unit 104 includes a reaction container 108, a reaction bath 112 within which the reaction container 108 is placed, a light source 117 and a spectral detector 118. Reaction solution, which is the mixture of the sample 106 and the reagent 109, is reserved within the reaction container 108.

In the analyzing unit 104, a light from the light source 117 is transmitted through the reaction solution, which is the mixture of the sample 106 and the reagent 109, within the reaction container 108 of the analyzing unit and is measured by the spectral detector 118 thereby to analyze the composition of the sample.

The stirring unit 105 includes the reaction container 108 and a piezo electric element 110. The piezo electric element 110 is driven by a driving circuit 120. The driving circuit 120 is controlled by the control unit 102. The veneration of the piezo electric element 110 is detected by a driving waveform detection unit. A detection signal from the driving waveform detection unit is sent to the control unit 102 thereby to control the operation of the piezo electric element 110.

The stirring unit 105 stirs the sample 106 ejected within the reaction container 108 from the sample housing unit 107 and the reagent 109.ejected within the reaction container 108 from the reagent housing unit 114 by ultrasonic waves generated by the piezo electric element 110.

The reaction containers 108 located at the stirring unit 105 and the analyzing unit 104 are soaked within heat reserving material 113 mainly formed by water reserved within the reaction bath 112 and kept at a constant temperature.

These reaction containers 108 are disposed on a reaction disc 115 and rotate or move together with the reaction disc 115 so as to reciprocally move between the stirring unit 105 and the spectral detector 118 when a reaction disc motor 116 is controlled by the control unit 102.

The reaction disc 115 includes the reaction bath 112 and has a disc-like shape. The reaction disc 115, which center portion is supported by the reaction disc motor 116, is driven by the reaction disc motor 116 and rotates.

The reaction containers 108 are disposed in a circular manner within the reaction bath 112 of the reaction disc 115.

The light emitted from the light source 117 transmits through the reaction container 108 and the reaction solution and is measured by the spectral detector 118. Of course, the light emitted from the light source 117 transmits through the reaction bath 112 and the water and so is measured by the spectral detector 118.

Although not shown in FIG. 1, a reaction container position detection means having the detection plates which number corresponds to the number of the reaction containers maybe provided so that the light measurement is performed synchronously while detecting the position of each of the reaction containers by the reaction container position detection means.

When the reaction container position detection means is provided, the detection plates, which number corresponds to the number of the reaction containers, are required and further a space for placing the detection plates and sensors for the detection plates is required. However, in this case, since the light measurement can be made while grasping the position of each of the reaction containers 108 by the reaction container position detection means, the light measurement procedure is facilitated.

Figure 2:
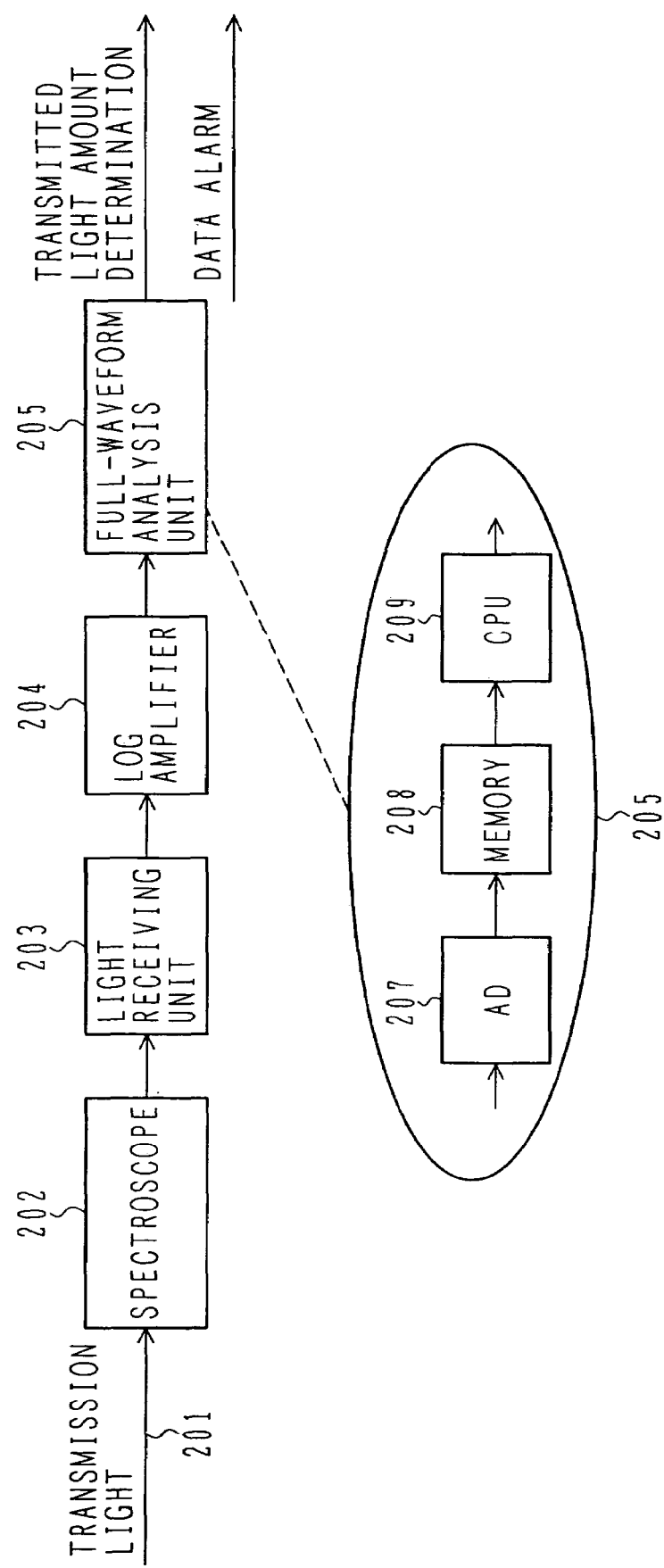
FIG. 2 is a block diagram for measuring absorbance and analyzing a full wave according to the embodiment of the present invention.

FIG. 2 is a block diagram for measuring the light intensity in the automatic analyzer according to the embodiment of the present invention.

The block diagram of the light intensity measurement section is configured by a spectral detector 202, a light receiving unit 203, a log amplifier 204 and a full-wave analysis unit 205.

The full-wave analysis unit 205 is configured by an analog-to-digital (A/D) converter 207, a memory device 208 and a CPU 209.

The transmission light 201 transmitted through the reaction solution are separated according to the wavelengths thereof by the spectral detector 202, then converted into voltages by the light receiving unit 203, then amplified by the log amplifier 204 and transmitted light amounts are determined by the full-wave analysis unit 205.

The unit 206 converts the amplified voltage data (light measurement data) into a digital value and temporarily stores in the memory device (memory) 208.

The CPU 209 analyzes the waveform data based on the light measurement data thus stored temporarily thereby to finally determine transmitted light amounts.

When an abnormal state is detected by the analysis of the waveform data, a data alarm etc. is outputted.

Figure 3:
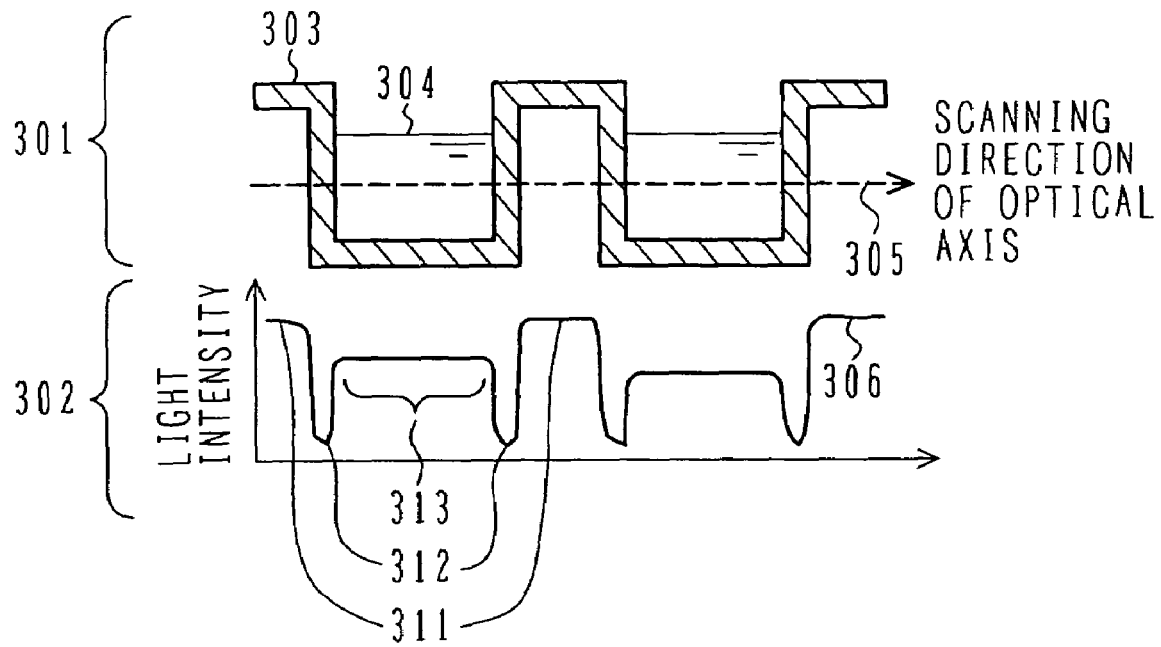
FIG. 3 is a diagram showing the relation between the positions of a reaction container and light intensities of transmission light according to the embodiment of the present invention.

FIG. 3 is a diagram for explaining the determination of the absorbance of the reaction solution and the position detection of the reaction container in the automatic analyzer according to the embodiment of the present invention.

FIG. 3 shows a section 301 of the reaction containers cut along the rotational direction thereof and also shows the changes of the light intensity 302 of the transmission light. The section 301 shows the section of the two adjacent reaction containers 303 cut along the rotational direction thereof. Each of the reaction containers 303 contains reaction solution 304 therein.

The optical axis of the transmission light is scanned in a direction 305 where the reaction solution 304 exists. Since the reaction containers 303 rotate in a state of being placed on the reaction disc 115, the optical axis of the transmission light is scanned so as to cross the reaction container.

As clear from the light measurement data shown by the changes 302, 306 of the light intensity of the transmission light measured by the spectral detector, the light intensity differs among a portion 311 where the reaction container does not exist, a wall portion (all is the wall) 312 of the reaction container and a portion 313 where the reaction solution exists.

The light intensity is high at the portion 311 where the reaction container does not exist since the degree of light absorbance is small. The light intensity is low at the wall portion (all is the wall) 312 of the reaction container since the degree of light absorbance is large. The light intensity is intermediate at the portion 313 where the reaction solution exists.

According to such the light measurement data shown by the change 306 of the light intensity, the light intensity at the portion 313 where the reaction solution exists is extracted and subjected to the calculation of the light intensity by the CPU 209 of the full-wave analysis unit 205, thereby to determine the absorbance of the reaction solution.

The light measurement shown by the change 306 of the light intensity is performed over the entire area from the one end to the other end of the reaction container. The CPU 209 calculates the light intensities based on the light measurement data of the entire area thereby to detect the position of the reaction container since the light intensity clearly differs between the wall portion (all is the wall) 312 of the reaction container and the portion 313 where the reaction solution exists. When such the position detection method of the reaction container using the software is employed, the reaction container position detection means using the detection plates can be eliminated.

The absorbance of the reaction solution obtained by the light intensity calculation of the CPU 209 represents an average value of the entirety of the reaction solution portion 313 (the area where the reaction solution exists) and so exhibits the absorbance with a high accuracy.

The measurement of the change 306 of the light intensity may be performed by scanning the optical axis so as to cross the reaction container obliquely, cross the reaction container in the vertical direction, or cross the reaction container at the upper portion, middle portion or lower portion thereof.

When the reaction container position detection means is also provided, the light measurement can be made as to a particular area of the reaction container 108. This arrangement is convenient in such a case where the measurement is made as to a particular reaction container again after the light measurement is made as to all the reaction containers.

Figure 4:
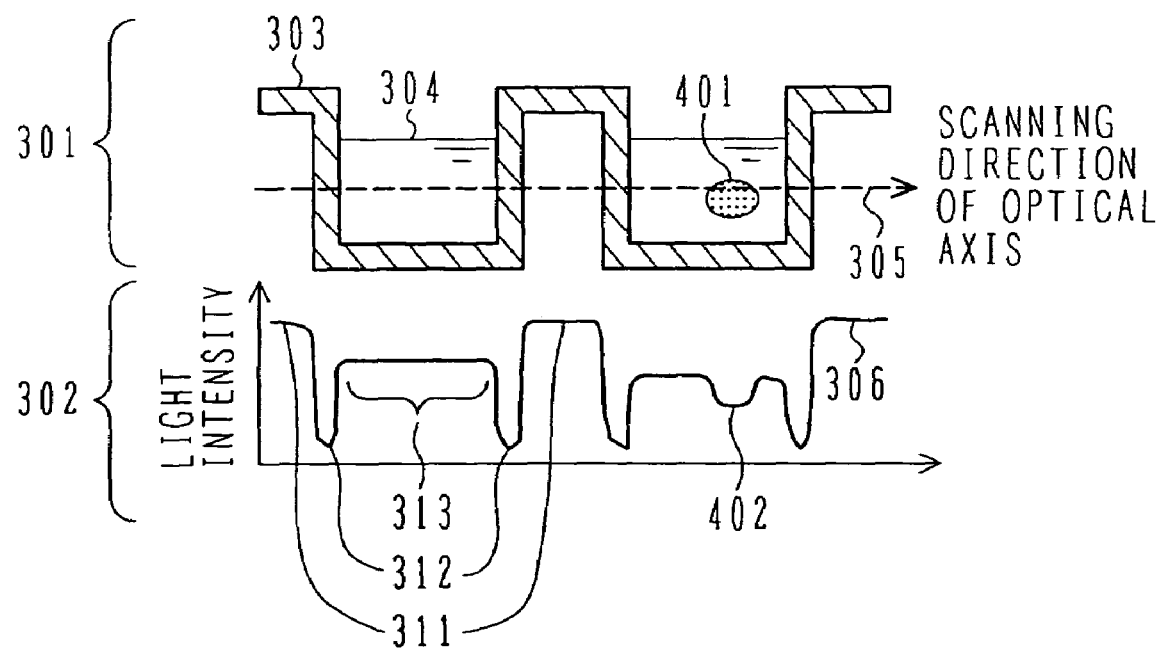
FIG. 4 is a diagram showing the relation between the positions of the reaction container and light intensities of transmission light in the case where a foreign matter is mixed, according to another embodiment of the present invention.

FIG. 4 is another embodiment of the present invention, in which a foreign matter within the reaction solution is detected by the full-wave analysis of the automatic analyzer.

When a foreign matter 401 such as a bubble exists on the scanning line 305 of the optical axis within the reaction solution 304, the transmission light is interfered by the foreign matter and so the light intensity reduces. When the foreign matter such as a bubble exists on the scanning line, the light intensity reduces like a portion 402 as shown by the change 306 of the light intensity, the foreign matter can be detected and displayed by analyzing the waveform of the change 306 of the light intensity.

Further, when the light intensity data of the foreign matter portion 402 is removed from the light intensity data of the reaction solution portion 313, the absorbance can be obtained without being influenced by the foreign matter. In this manner, when the light measurement data obtained by measuring over the entire area from the one end to the other end of the reaction container is used, the absorbance can be determined with a high accuracy irrespective of the presence or non-presence of a foreign matter.

Figure 5:
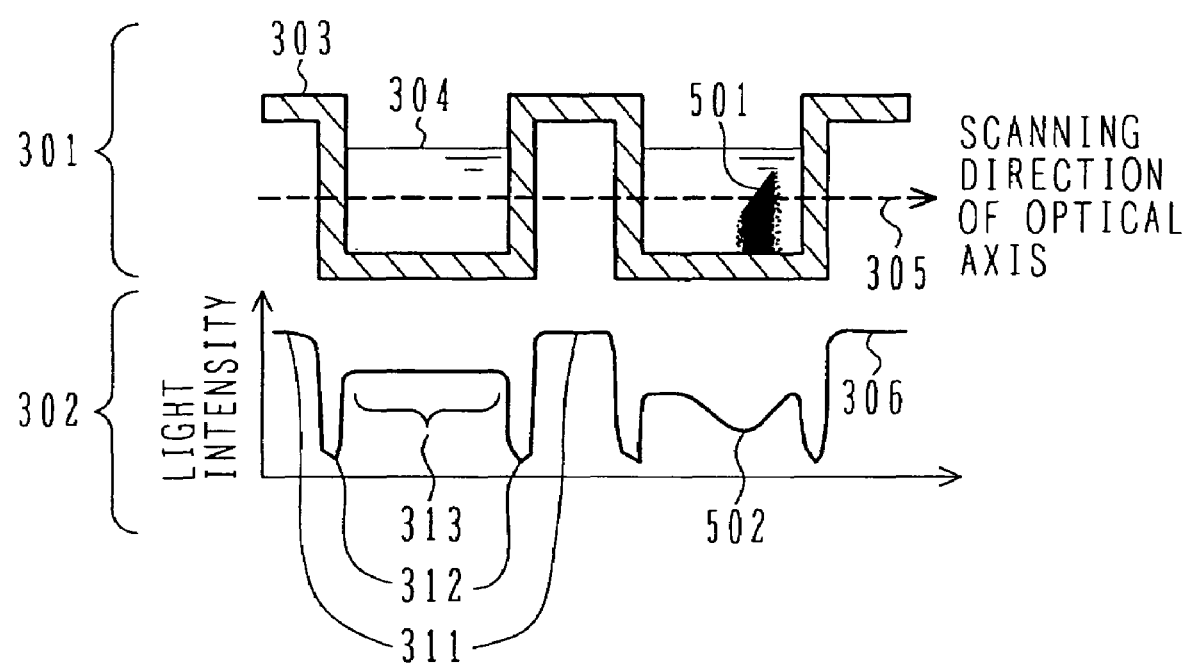
FIG. 5 is a diagram showing the relation between the positions of the reaction container and light intensities of transmission light in the case where a reagent is not mixed sufficiently, according to still another embodiment of the present invention

FIG. 5 is still another embodiment of the present invention, in which a mixing state of the reaction solution is detected by the full-wave analysis of the automatic analyzer.

When there is a portion 501 where the reagent etc. is not mixed on the scanning line 305 of the optical axis within the reaction solution 304, the light intensity at this portion differs from the light intensity at a portion where the reagent is mixed. When the portion 501 where the reaction solution is not sufficiently mixed exists on the scanning line, the light intensity reduces like a portion 502 as shown by the change 306 of the light intensity, the insufficient mixture of the reaction solution can be detected and displayed by analyzing the waveform of the change 306 of the light intensity.

This display can be made by a display means for displaying the mixing state of the reagent. When it is determined that the mixture of the reaction solution is insufficient, it can be an index for the operation such as a re-stirring.

What is claimed is:
1. An automatic analyzer comprising:
a reaction container containing reaction solution therein;
a light source emitting light to be transmitted through the reaction solution;
a spectral detector measuring the light intensity of the light transmitted through the reaction solution, said spectral detector measuring the light intensity of the light over an entirety of an area from one end to the other end of the reaction container at a portion where the reaction solution is contained;
a memory storing light intensity data measured by the spectral detector; and
a CPU analyzing the light intensity data stored in the memory, said light intensity data being detected at areas where the reaction solution exists, and detecting a foreign matter in the reaction solution on the basis of reduction of the light intensity.

2. An automatic analyzer according to claim 1, wherein said CPU analyzes the light intensity data stored in the memory except for the light intensity data obtained through said foreign matter within the reaction solution.

3. An automatic analyzer according to claim 1, further comprising display means displaying presence or non-presence of a foreign matter or displays a mixing state of reagent within the reaction solution.

4. An automatic analyzer comprising:
a reaction container containing reaction solution therein;
a light source emitting light to be transmitted through the reaction solution;
a spectral detector measuring the light intensity of the light transmitted through the reaction solution, said spectral detector measuring the light intensity of the light over an entirety of an area from one end to the other end of the reaction container at a portion where the reaction solution is contained;
a memory storing light intensity data measured by the spectral detector; and
a CPU analyzing the light intensity data stored in the memory, said light intensity data being detected at areas where the reaction solution exists, and detecting insufficient mixture of the reaction solution on the basis of reduction of the light intensity.

5. An automatic analyzer according to claim 4, further comprising a display means for displaying insufficient mixture of the reaction solution.

6. An automatic analyzer according to claim 4, further comprising a stirring unit for stirring a mixture of the reaction solution of said insufficient mixture of the reaction solution.

\* \* \* \* \*